(12) United States Patent
Flanders

(10) Patent No.: US 9,084,539 B2
(45) Date of Patent: Jul. 21, 2015

(54) WIRELESS PRESSURE WIRE SYSTEM WITH INTEGRATED POWER

(75) Inventor: Dale C. Flanders, Lexington, MA (US)

(73) Assignee: Volcano Corporation, San Diego, CA (US)

( * ) Notice: Subject to any disclaimer, the term of this patent is extended or adjusted under 35 U.S.C. 154(b) by 628 days.

(21) Appl. No.: 13/364,972

(22) Filed: Feb. 2, 2012

(65) Prior Publication Data

US 2013/0204111 A1 Aug. 8, 2013

(51) Int. Cl.
| | |
|---|---|
| *A61B 5/0215* | (2006.01) |
| *H01M 6/20* | (2006.01) |
| *A61B 5/00* | (2006.01) |
| *A61B 5/01* | (2006.01) |
| *A61B 5/026* | (2006.01) |
| *H01M 6/32* | (2006.01) |

(52) U.S. Cl.
CPC ............ *A61B 5/0215* (2013.01); *A61B 5/0002* (2013.01); *A61B 5/01* (2013.01); *A61B 5/026* (2013.01); *A61B 5/0008* (2013.01); *A61B 2560/0214* (2013.01); *H01M 6/32* (2013.01)

(58) Field of Classification Search
CPC .......... A61B 5/01; A61B 5/026; A61B 5/027; A61B 5/0215; H01M 6/30; H01M 6/32
USPC .................. 600/407, 481, 486, 505
See application file for complete search history.

(56) References Cited

U.S. PATENT DOCUMENTS

| | | | |
|---|---|---|---|
| 3,878,830 A * | 4/1975 | Bicher ......................... 600/360 |
| 6,264,611 B1 * | 7/2001 | Ishikawa et al. .............. 600/486 |
| 6,471,656 B1 | 10/2002 | Shalman et al. |
| 6,565,514 B2 | 5/2003 | Svanerudh et al. |
| 6,708,050 B2 * | 3/2004 | Carim ........................... 600/372 |
| 6,844,108 B1 * | 1/2005 | Lee et al. ...................... 429/116 |
| 7,695,840 B2 * | 4/2010 | Bartling ........................ 429/483 |

(Continued)

FOREIGN PATENT DOCUMENTS

| | | |
|---|---|---|
| WO | 00/32105 A1 | 6/2000 |
| WO | 01/21057 A2 | 3/2001 |

(Continued)

OTHER PUBLICATIONS

International Search Report, mailed Jun. 17, 2013, from counterpart International Application No. PCT/US2013/022863 filed Jan. 24, 2013.

(Continued)

*Primary Examiner* — Navin Natnithithadha
*Assistant Examiner* — Meredith Weare
(74) *Attorney, Agent, or Firm* — Haynes and Boone, LLP

(57) ABSTRACT

A sensor wire system with an integrated power source and wireless transmission is provided. A sensor wire includes a distal end that is inserted into a blood vessel of a patient's body. A sensor that is mounted at the distal end of the sensor wire and an electronics unit of the distal end of the sensor wire transmit information generated by the sensor to a receiver unit outside of the patient's body wirelessly. The system further includes a power source, which in one example is mounted to the distal end of the sensor wire, that supplies power to the electronics unit. Preferably the wire body functions as an antenna for the wireless broadcasting.

23 Claims, 5 Drawing Sheets

(56) References Cited

U.S. PATENT DOCUMENTS

| | | | |
|---|---|---|---|
| 2003/0187339 A1* | 10/2003 | Carim | 600/372 |
| 2006/0189845 A1* | 8/2006 | Maahs et al. | 600/146 |
| 2007/0276444 A1* | 11/2007 | Gelbart et al. | 607/6 |
| 2008/0109054 A1* | 5/2008 | Hastings et al. | 607/127 |
| 2008/0137092 A1 | 6/2008 | Kraemer et al. | |
| 2008/0138696 A1* | 6/2008 | Bartling | 429/42 |
| 2009/0082678 A1* | 3/2009 | Smith | 600/486 |
| 2010/0042010 A1* | 2/2010 | Dekker et al. | 600/523 |
| 2010/0210955 A1* | 8/2010 | Forsell | 600/486 |
| 2010/0234698 A1* | 9/2010 | Manstrom et al. | 600/301 |
| 2010/0305476 A1* | 12/2010 | Thornton et al. | 600/585 |

FOREIGN PATENT DOCUMENTS

| | | |
|---|---|---|
| WO | 03/022122 A2 | 3/2003 |
| WO | 2006/045075 A1 | 4/2006 |
| WO | 2008/075295 A1 | 6/2008 |
| WO | 2010/030882 A1 | 3/2010 |
| WO | 2010/033971 A1 | 3/2010 |

OTHER PUBLICATIONS

"Reserve battery" (http://en.wikipedia.org/wiki/Reserve_battery).

* cited by examiner

WIRELESS PRESSURE WIRE SYSTEM WITH INTEGRATED POWER

BACKGROUND OF THE INVENTION

Heart disease is a leading cause of death for men and women in the United States. Consequently, there are numerous medications, medical procedures, and medical devices aimed at diagnosing and treating heart disease.

One type of medical procedure aimed at diagnosing heart disease is angiography. The procedure requires injecting a contrast agent into the blood stream and then taking x-rays to determine if there is a blockage within the blood vessel. A problem with an angiography is that the procedure can only determine if a blockage exists, but not whether the blockage is actually affecting the blood flow within the blood vessel. As a result, many patients elect to have unnecessary procedures to treat the blockage without confirming the severity of the blockage.

Another procedure for assessing heart disease is fractional flow reserve (FFR). FFR is a technique used in coronary catheterization to measure the pressure difference and thus blood flow across a partially blocked or constricted artery. Using a guidewire system, measurements are taken on both sides of a blockage within a blood vessel to determine if there is a pressure gradient or reduced blood flow due to the blockage. If there is no drop in pressure (or a nominal drop), then there may be no need for further medical intervention because the blockage is not significantly impeding the flow of blood. Conversely, if there is a significant drop across the blockage, then the blockage may need to be removed or treated because the blood flow is impaired by the blockage.

Generally, the FFR procedure is performed by inserting a guidewire system into the femoral or radial artery of the patient. The guidewire is maneuvered into position within a partially blocked blood vessel, and a sensor at the distal end of the guidewire is used to measure pressure, temperature, and/or blood flow to determine the severity of the blockage. The sensor is connected to a display device such as a monitor of a computer screen to display the patient's readings during the procedure.

SUMMARY OF THE INVENTION

A problem with some sensor devices is that they must be physically connected to both a power source and display device during the procedure. These requirements limit the range and mobility during the procedure and create wire management challenges. They require the operator to manipulate the sensor devices so that they are properly located in the patient. The electrical connectors must be uncovered or cleaned for connection to display and data processing devices. This adds extra steps and may involve breaches of the procedure's sterile field.

The present invention is directed to a preferably single-use sensor wire system and method that can have both an integrated power source and integrated antenna for wireless transmission.

In general according to one aspect, the invention features a sensor wire system. It comprises a sensor wire body having a distal end that is inserted into a blood vessel of a patient, a sensor that is mounted at the distal end of the sensor wire body, an electronics unit of the distal end of the sensor wire body that wirelessly transmits information generated by the sensor to a receiver unit outside of the patient, and a power source that supplies power to the electronics unit.

In preferred embodiments, the sensor is a pressure sensor, a temperature sensor, and/or a blood flow sensor. In other examples, it is an imaging device, such as an IVUS, FLIVUS, OCT, spectroscopic, ICE, or forward looking ICE analysis device, with encoded images from the imaging device being broadcast to the receiver unit.

In one embodiment, the power source is a power harvesting device, such as one that converts the cyclic pressure changes of surrounding blood into power to the electronics unit. In other cases, the power source is a battery, such as a battery that is activated upon insertion into the patient and that powers the electronics unit until the power source is depleted.

In general according to another aspect, the invention features a method of using a sensor wire. This comprises inserting a sensor wire body having a distal end into a blood vessel of a patient, mounting a sensor to the distal end of the sensor wire body, supplying power to an electronics unit, and transmitting information generated by the sensor to a receiver unit via the electronics unit.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
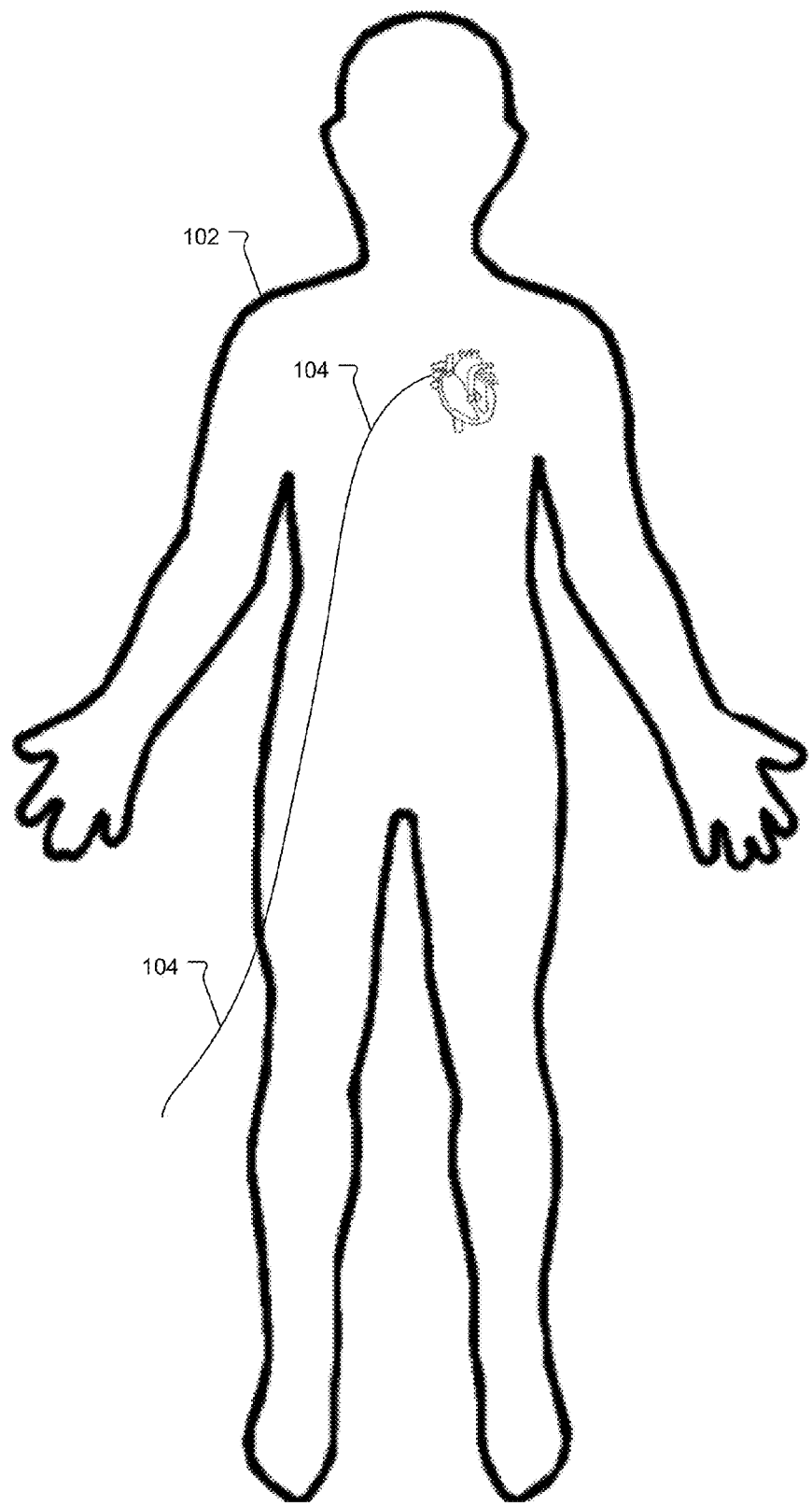
FIG. 1 is a schematic illustration showing a sensor wire inserted into a patient's body.

FIG. 1 is an illustration of a sensor wire 104 that is inserted into a patient's body 102.

In operation, the sensor wire system 104 is inserted into the artery, such as the femoral artery, of a patient 102 and guided through the blood vessels until arriving at a potentially partially blocked blood vessel of interest within the patient's body 102, such as a coronary artery. In alternative embodiments, the sensor wire 104 is inserted via the radial or other artery, or vein. In other applications, other arteries or veins are the vessels of interest.

Figure 2:
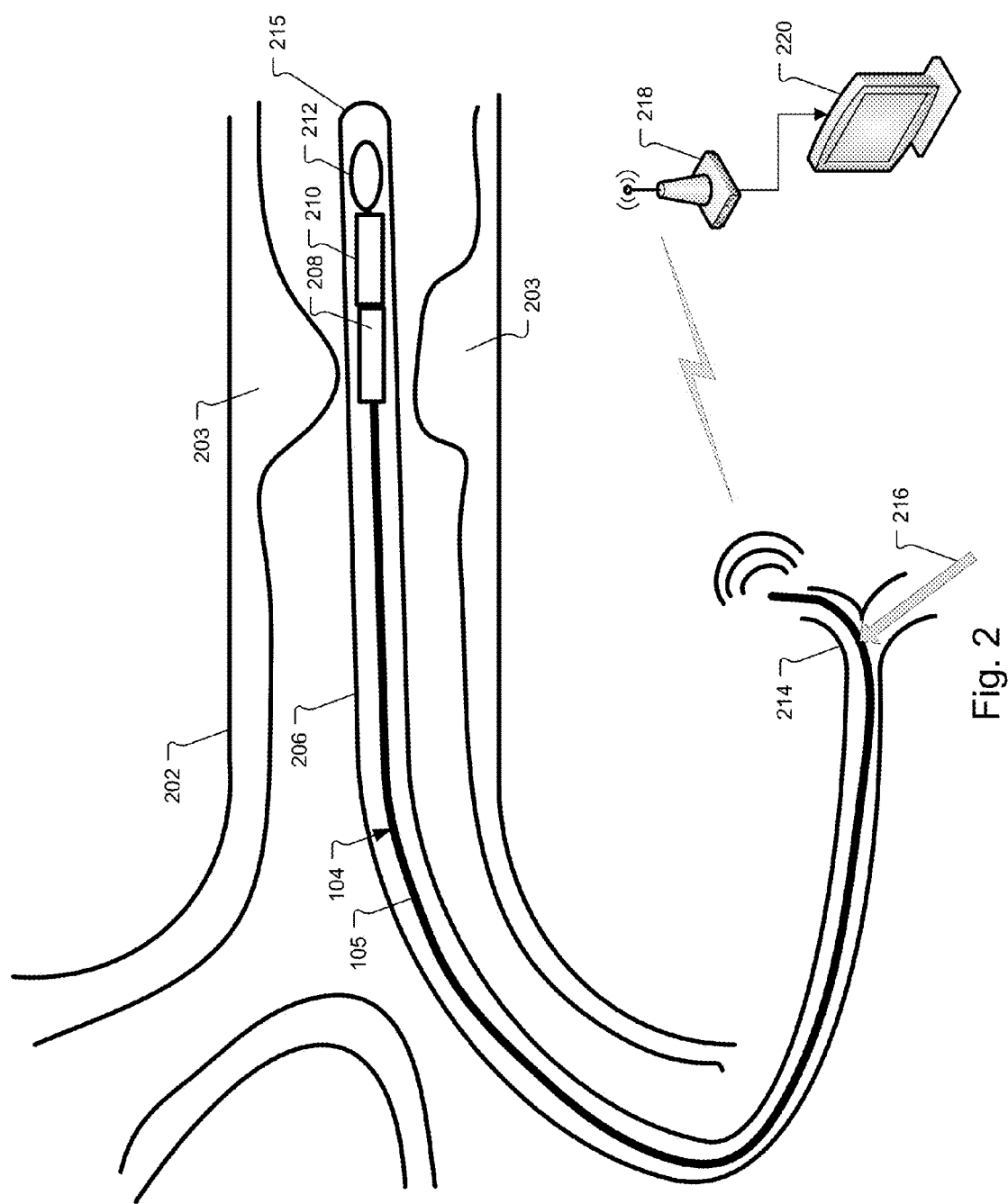
FIG. 2 schematic cross-sectional view showing a sensor wire within a partially blocked blood vessel of a patient that is wirelessly transmitting information to a receiver.

FIG. 2 illustrates the sensor wire system 104 within a partially blocked blood vessel of a patient 102 that is wirelessly transmitting information to a receiver 218. In one embodiment, the sensor wire 104 measures pressure, blood flow, and/or temperature within the blood vessel 202 of the patient 102. Typically, the distal end 215 of the sensor wire system 104 is inserted through the femoral artery and guided to the blocked blood vessel 202 by holding the sensor wire body. Steering the sensor wire 104 within the blood vessels is often performed by manually manipulating the proximal end 214 of the sensor wire body 105 or using a separate guide wire.

Once in position, the sensor 212 measures pressure, blood flow and/or temperature and encodes the information in the form of electrical signals. In a preferred embodiment the sensor 212 includes a pressure transducer, a flow detector, and a temperature transducer.

In other embodiments, the sensor 212 further includes an imaging system. In one example, the sensor 212 included an intravascular ultrasound (IVUS) device. In another variant, the sensor 212 includes a forward-looking IVUS (FLIVUS) device. In still other embodiments, the sensor 212 includes optical coherence tomography (OCT), near infrared spectroscopic, intracardiac echocardiography (ICE), and forward looking ICE devices.

The electrical signals generated by the sensor 212 are relayed to the electronics unit 210, which processes the signals. The information is then wirelessly transmitted to an external receiver 218. The sensor wire body 105 is preferably fabricated from conductive materials such that the sensor wire body 105 operates as a radio frequency antenna capable of broadcasting the information to the external receiver 218.

Depending on the implementation, the sensor signals broadcast from the antenna are the encoded time-varying pressure, flow, and temperature detected by the sensor 212.

In the cases where the sensor 212 includes an imaging modality, the broadcast sensor signals are encoded images from the IVUS, FLIVUS, OCT, spectroscopic, ICE, or forward looking ICE analysis.

Additionally, a power source 208 of the sensor wire system 104 supplies power to the electronics unit 210 and possibly the sensor 212 depending on the sensor technology used. In a typical implementation, the power source is a battery. However, in other embodiments, one or more storage capacitors supply the power requirements.

In a one embodiment, the battery power source 208 includes an anode and a cathode, but initially lacks the necessary electrolyte needed to complete a battery. In operation, the power source 208 is activated by injecting an electrolyte 216 into the sensor wire 104 or between the sensor wire 104 and a surrounding protective sheath. The electrolyte reacts with the anode and cathode to create a battery. Once the power source 210 is activated, the sensor wire system 104 wirelessly transmits the information generated by the sensor 212 until the power source 208 is exhausted.

In still another embodiment, the power for the electronics unit 210 is provided by a power harvesting system that converts the biological motion of the patient into power. In one example, the power source 208, or possibly the sensor wire body 105 itself, includes a piezo-electric power source that converts the cyclic pressures changes of the surrounding blood into electricity that powers the electronics unit 210.

The receiver 218 is connected to a display device 220 that displays the information on a screen. The display device is part of a computer system or medical workstation that includes a storage medium and printer to generate a printout of the information as well as to store a copy for future analysis.

Figure 3:
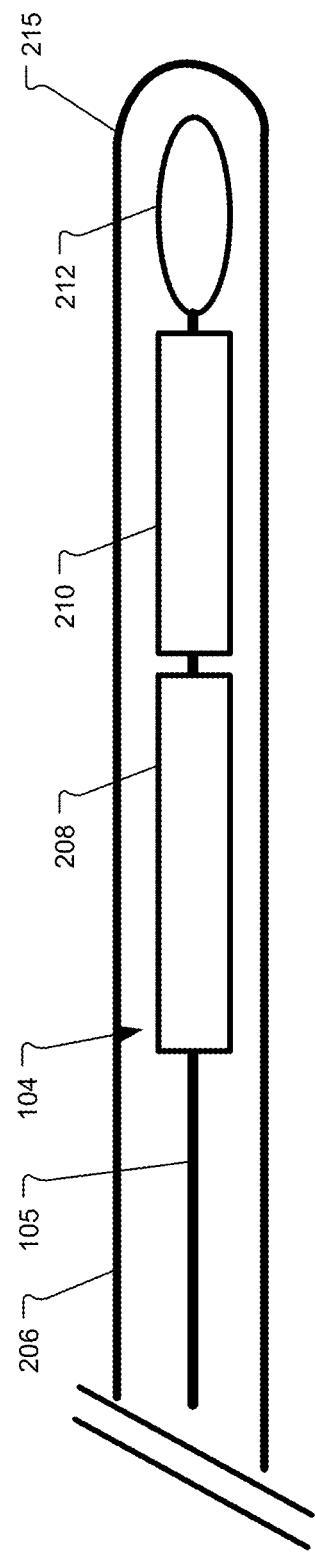
FIG. 3 is schematic cross-sectional view showing the distal end of a sensor wire with a protective sheath.

FIG. 3 is an illustration of the distal end of a sensor wire 104 with a protective sheath 206.

In a preferred embodiment, the sensor wire 104 is contained within a protective sheath 206. The sheath 206 isolates the sensor 212, electronics unit 210 and power source 208, and wire body 105 from the patient's body 102. In alternative embodiments, however, the sensor wire 104 will not have a protective sheath.

Figure 4:
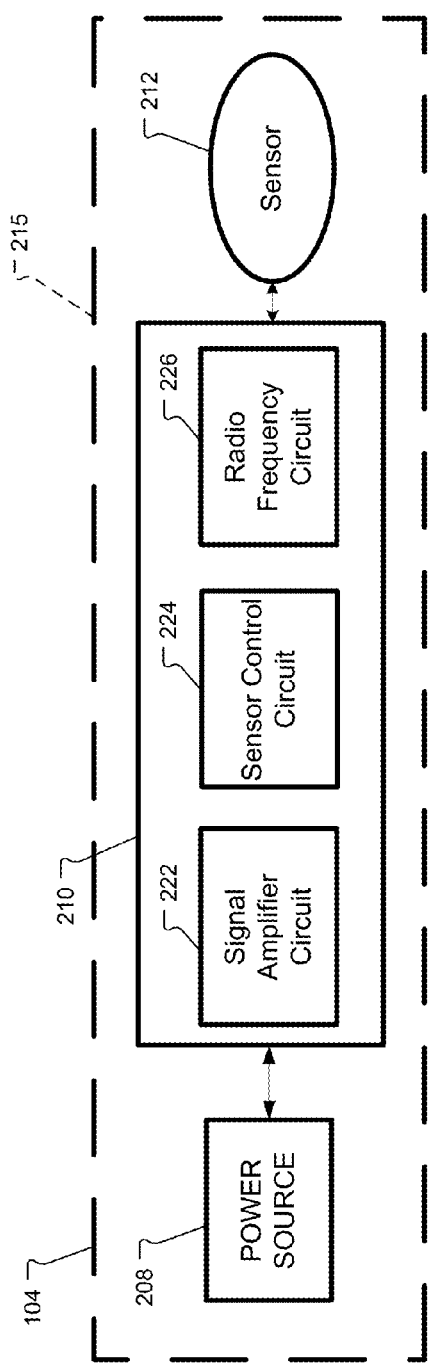
FIG. 4 is a block diagram of the electronics unit in the distal end of the sensor wire.

FIG. 4 is a block diagram of the electronics unit 210 in the distal end 215 of the sensor wire system 104.

In a preferred embodiment, the sensor 212 is located in the tip of the distal end of the sensor wire 104. The sensor 212 generates pressure, blood flow and/or temperature information, usually in the form of electrical signals generated by a transducer. The electrical signals from the sensor 212 are sent to the electronics unit 210. The electrical signals are processed by the sensor control circuit 224 and encoded for transmission to the external receiver 218 and displayed on the screen 220.

The radio frequency (RF) circuit 226 is designed to wirelessly broadcast the information via the sensor wire body 105 at a specific frequency. In an alternative embodiment, the RF circuit allows the frequency to be varied so that multiple sensor wires operate at different frequencies in close spectral proximately without creating interference.

The electronics control unit 210 further includes a signal amplifier circuit 222 to amplify the signal prior to being wirelessly broadcast to the receiver 218.

An added benefit is that the sensor wire 104 can be used as a guidewire. Catheters can be threaded over the sensor wire 104. This process is facilitated by the fact that there are no electrical connections to the external receiver.

Figure 5:
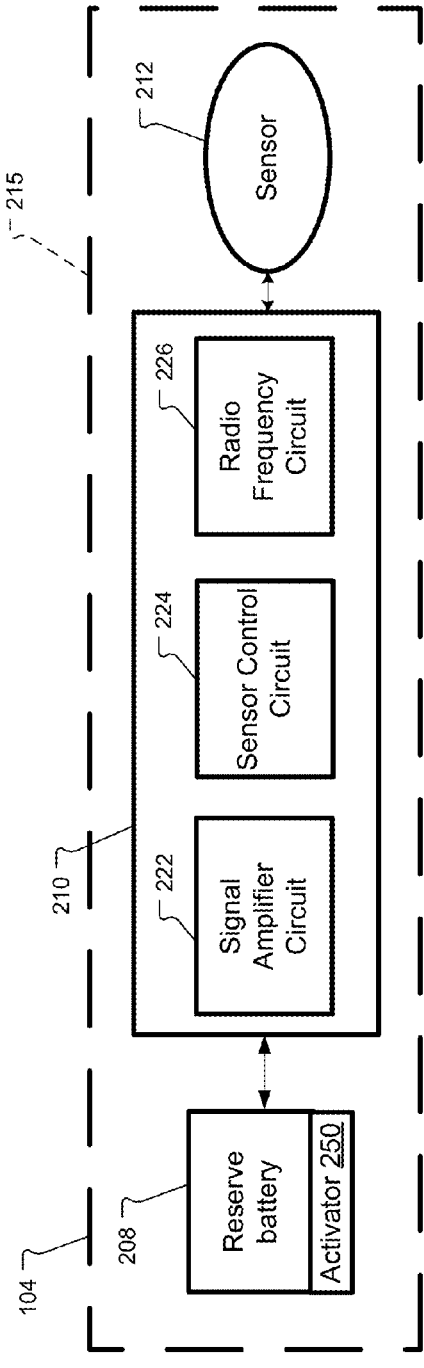
FIG. 5 is a block diagram of the electronics unit in the distal end of the sensor wire according to another embodiment using a reserve battery power source.

FIG. 5 is a block diagram of the electronics unit 210 in the distal end 215 of the sensor wire system 104 according to another embodiment.

In this example, the power source 208 is a reserve battery. These are devices that are commonly used in ordinance, for example. Reserve batteries are activated by addition of material or a change in temperature, the activator 250. With this addition or change, then the reserve battery 208 delivers current for several minutes to hours.

In one example, the activator 250 is water or other fluid that functions as an electrolyte causing the battery 208 to begin delivering current and thus power the electronics unit 210. The medical professional, in one example, injects the activator material 250 into the battery or breaks a bladder or capsule filled with the material, which then flows into the battery. In another example the activator is a gas that is either the active cathode material or part of the electrolyte.

Figure 6:
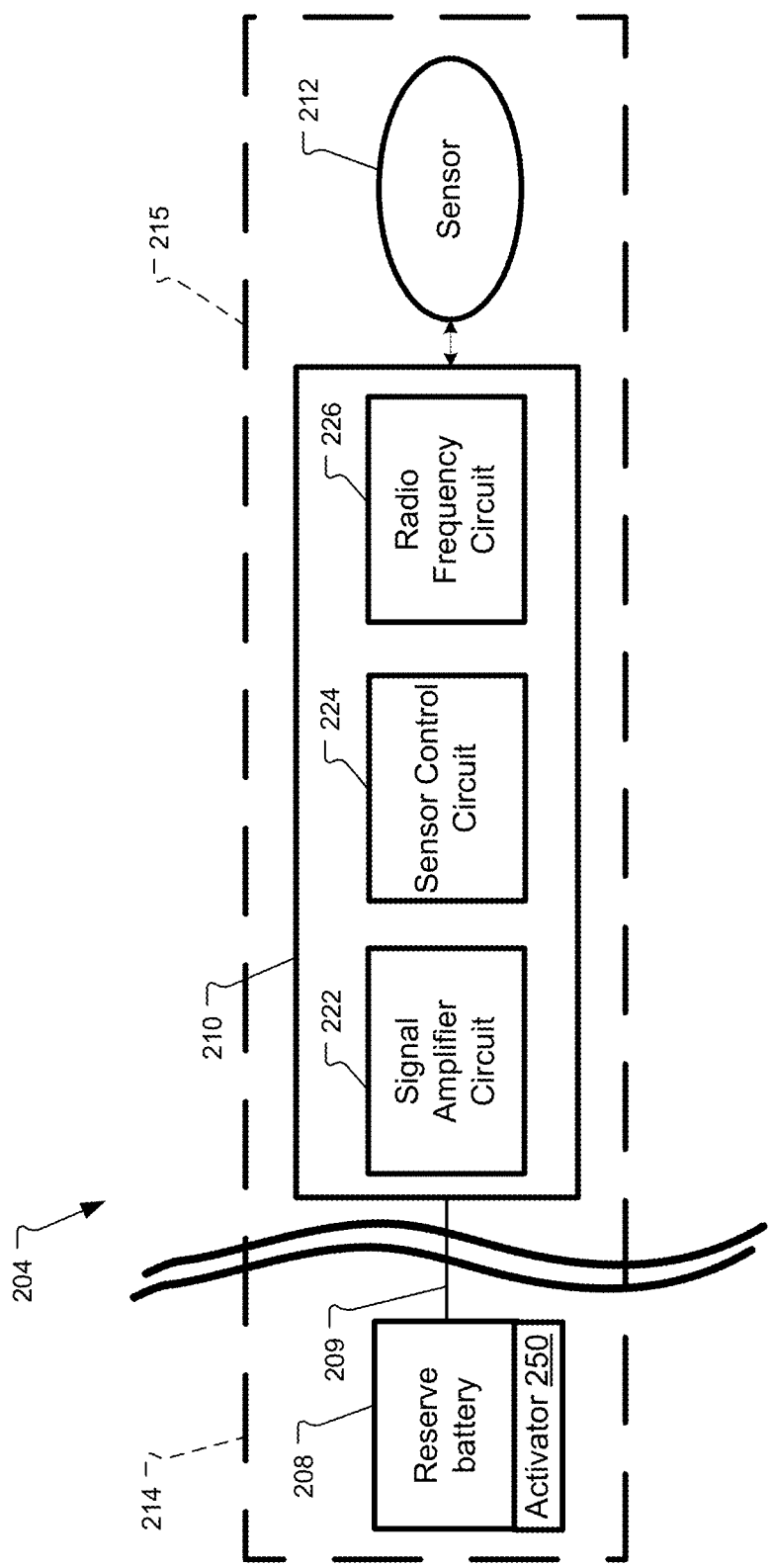
FIG. 6 is a block diagram of the electronics unit in the distal end of the sensor wire with a battery power source at the proximal end.

FIG. 6 is a block diagram of the electronics unit 210 in the distal end 215 of the sensor wire system 104 according to another embodiment, in which the reserve battery 208 is located at the proximal end 215 of the sensor wire system 104. This embodiment has the advantage that the reserve battery 208 can be activated by the operator/surgeon only after the wire system 104 has been placed in the patient. Wires 209 extending through the system 104 carry the current from the reserve battery 208 at the proximal end 214 to the electronics unit 210 at the distal end 215.

In another example, the reserve battery 208 is wire shaped extending through the length of the sensor wire system 104. In some examples, the wire-shaped reserve battery provides mechanical support for the system 104.

While this invention has been particularly shown and described with references to preferred embodiments thereof, it will be understood by those skilled in the art that various changes in form and details may be made therein without departing from the scope of the invention encompassed by the appended claims.

What is claimed is:

1. A sensor wire system, comprising:
    a sensor wire body having a distal end adapted to be inserted into a blood vessel of a patient;
    a sensor that is mounted at the distal end of the sensor wire body;
    an electronics unit of the sensor wire body that wirelessly transmits information generated by the sensor to a receiver unit outside of the patient; and
    a power source that supplies power to the electronics unit;
    wherein the power source includes an anode, a cathode, and a protective sheath extending along a length of the sensor wire body and surrounding the anode and the cathode, wherein the protective sheath is configured to receive an electrolyte that reacts with the anode and the cathode to create a battery at the time of use.

2. The system according to claim 1, wherein the sensor is a pressure sensor.

3. The system according to claim 1, wherein the sensor is a temperature sensor.

4. The system according to claim 1, wherein the sensor is a blood flow sensor.

5. The system according to claim 1, wherein the sensor is an imaging device.

6. The system according to claim 1, wherein the electronics unit further comprises a signal amplifier, sensor control circuit, and radio frequency circuit.

7. The system according to claim 1, wherein the power source is a battery.

8. The system according to claim 1, wherein the electronics unit transmits the information until the power source is depleted.

9. The system according to claim 1, wherein the battery is disposed at a proximal end or the distal end of the sensor wire body.

10. A sensor wire system, comprising:
    a sensor wire body having a distal end adapted to be inserted into a blood vessel of patient;
    a sensor that is mounted at the distal end of the sensor wire body;
    an electronics unit that transmits information generated by the sensor, via the sensor wire body that functions as a radio frequency antenna, to a receiver unit outside of the patient; and
    a power source that supplies power to the electronics unit;
    wherein the power source includes an anode, a cathode, and a protective sheath extending along a length of the sensor wire body and surrounding the anode and the cathode, wherein the protective sheath is configured to receive an electrolyte that reacts with the anode and the cathode to create a battery at the time of use.

11. The system according to claim 10, wherein the sensor is at least one of a pressure sensor, a temperature sensor, a blood flow sensor, or an imaging device.

12. The system according to claim 10, wherein the electronics unit further comprises a signal amplifier, sensor control circuit, and radio frequency circuit.

13. The system according to claim 10, wherein the battery is disposed at a proximal end or the distal end of the sensor wire body.

14. A method of using a sensor wire, comprising:
    inserting a sensor wire body having a distal end into a blood vessel of a patient in which a sensor is mounted to the distal end of the sensor wire body, the sensor wire body further including an electronics unit communicatively coupled to the sensor;
    creating a battery utilized to supply power to the electronics unit at the time of use; the battery including an anode, a cathode, and a protective sheath extending along a length of the sensor wire body, and wherein creating the battery includes introducing an electrolyte into the protective sheath such that the electrolyte reacts with the anode and the cathode;
    supplying the power to the electronics unit; and
    transmitting information generated by the sensor to a receiver unit via the electronics unit.

15. The method according to claim 14, wherein the sensor is a pressure sensor.

16. The method according to claim 14, wherein the sensor is a temperature sensor.

17. The method according to claim 14, wherein the sensor is a blood flow sensor.

18. The method according to claim 14, further comprising displaying the information generated by the sensor on a display device.

19. The method according to claim 14, further comprising the sensor generating images of the blood vessel.

20. The method according to claim 14, wherein the electronics unit transmits the information until the battery is depleted.

21. The method according to claim 14, wherein creating the battery includes creating the battery at a proximal end or the distal end of the sensor wire body.

22. The method according to claim 14, wherein introducing an electrolyte includes injecting the electrolyte between the sensor wire and the protective sheath.

23. The method according to claim 14, wherein introducing an electrolyte includes breaking a reservoir of the electrolyte such that the electrolyte flows into the protective sheath.

* * * * *